(12) United States Patent  
Zaman et al.

(10) Patent No.: US 6,963,076 B1  
(45) Date of Patent: Nov. 8, 2005

(54) SYSTEM AND METHOD FOR OPTICALLY SENSING DEFECTS IN OPC DEVICES

(75) Inventors: Kamran Uz Zaman, Pittsford, NY (US); L. John Potter, Fairport, NY (US); Stanley J. Pietrzykowski, Jr., Rochester, NY (US)

(73) Assignee: Xerox Corporation, Stamford, CT (US)

( * ) Notice: Subject to any disclaimer, the term of this patent is extended or adjusted under 35 U.S.C. 154(b) by 62 days.

(21) Appl. No.: 09/629,204

(22) Filed: Jul. 31, 2000

(51) Int. Cl.[7] ............................................. G01N 21/88
(52) U.S. Cl. ............................. 250/559.4; 250/559.45; 356/237.2; 382/141
(58) Field of Search ...................... 250/559.45–559.49, 250/559.04–559.06, 559.4, 559.41, 559.36; 382/141, 145, 149, 152, 108; 356/237.2, 356/237.3, 237.1, 240.1

(56) References Cited

U.S. PATENT DOCUMENTS

| | | | | |
|---|---|---|---|---|
| 4,066,363 A | * | 1/1978 | Juvinall | 356/428 |
| 4,148,065 A | * | 4/1979 | Nakagawa et al. | 348/129 |
| 4,641,966 A | * | 2/1987 | Lemmers et al. | 356/237.2 |
| 4,748,335 A | * | 5/1988 | Lindow et al. | 250/559.22 |
| 5,040,228 A | * | 8/1991 | Bose et al. | 382/141 |
| 5,118,193 A | * | 6/1992 | Brown et al. | 356/237.1 |
| 5,153,444 A | * | 10/1992 | Maeda et al. | 250/559.05 |
| 5,157,463 A | * | 10/1992 | Brown et al. | 356/394 |
| 5,352,329 A | * | 10/1994 | Herbert et al. | 216/83 |
| 5,517,235 A | * | 5/1996 | Wasserman | 382/147 |
| 6,069,971 A | * | 5/2000 | Kanno et al. | 382/144 |
| 6,118,540 A | * | 9/2000 | Roy et al. | 356/394 |
| 6,487,307 B1 | * | 11/2002 | Hennessey et al. | 382/149 |
| 2001/0012392 A1 | * | 8/2001 | Langley | 382/145 |

FOREIGN PATENT DOCUMENTS

| | | | | |
|---|---|---|---|---|
| JP | 03291552 A | * | 12/1991 | G01N 21/88 |
| WO | WO 99/16010 | * | 4/1999 | G06K 9/00 |

* cited by examiner

*Primary Examiner*—Edward J. Glick  
*Assistant Examiner*—Chih-Cheng Glen Kao  
(74) *Attorney, Agent, or Firm*—Perman & Green, LLP

(57) ABSTRACT

A system for optically sensing manufacturing defects in organic photo conductor (OPC) devices. The system comprising an illumination source for illuminating the OPC device; at least one optical sensor positioned to view the illuminated device; and a controller connectable to the optical sensor, the controller comprising a threshold detector for determining manufacturing defects.

27 Claims, 6 Drawing Sheets

SYSTEM AND METHOD FOR OPTICALLY SENSING DEFECTS IN OPC DEVICES

BACKGROUND OF THE INVENTION

1. Field of the Invention

The present invention relates to optically sensing manufacturing defects in organic photo conductors (OPC) and, more particularly, to detecting bottom edge wipe in the manufacture of OPCs.

2. Prior Art

Cylindrical aluminum organic photo conductor (OPC) substrates undergo dip-coating process by vertically immersing the cylindrical OPC in a dip tank. After dipping it is required that the trailing edge of the part must meet certain specifications in order to avoid bottom edge wipe defects (i.e., where dip coating residue remains on the bottom of the OPC). FIG. 5 shows that bottom edge wipe (BEW) defects are the most common of defects caused by the dipping process. However, existing automatic visual inspection (AVI) systems are not designed to inspect for BEW defects. The existing AVI systems only inspect for defects within the image area of the OPC and ignores the areas outside the image area, i.e., the bottom edge area. Yet, the interface of the bottom edge area within larger systems and subsystems is critical to the performance of such systems. For this reason, the OPC bottom edge area is subjected to an outgoing quality control, but not until after value is added to the defective OPC at several other stages in the manufacturing process prior to the quality control check. Thus, the failure to detect BEW defects early in the manufacturing process results in decreased productivity as well as lost value.

SUMMARY OF THE INVENTION

In accordance with one embodiment of the invention, a system for optically sensing manufacturing defects in OPC devices is provided. The system comprising an illumination source for illuminating an OPC device; at least one optical sensor positioned to view the illuminated device; and a controller connectable to the optical sensor, the controller comprising a threshold detector for detecting manufacturing defects.

Another aspect of the invention is a method for optically classifying residues on at least one bottom area of a OPC. The method comprising the steps of: illuminating the at least one bottom area of the OPC; capturing reflected illumination from at least one illuminated bottom area of the OPC device; comparing the captured reflected illumination with at least one threshold level; and classifying at least one bottom area of the OPC device based upon the comparison of the captured reflected illumination with the at least one threshold level.

Another aspect of the invention is a method for optically discriminating an Organic Photo Conductor (OPC) device. The method comprising the steps of illuminating a bottom area of the OPC device; sensing reflected light from the illuminated OPC bottom area; and comparing reflected light with a threshold level to determine if a defect exist.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
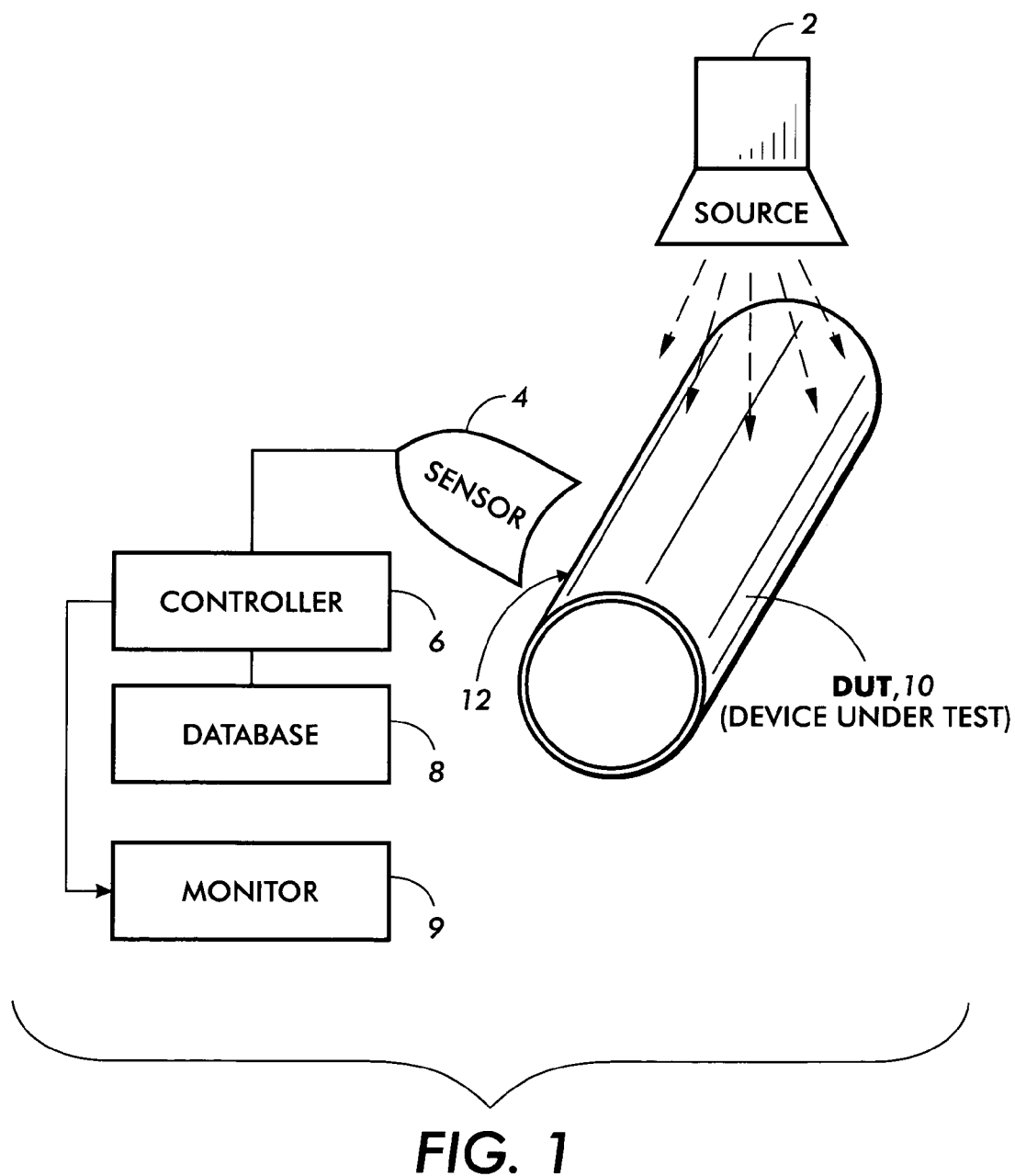
FIG. 1 is a schematic diagram of one embodiment of the invention.

Referring to FIG. 1, there is shown an exploded perspective view of a bottom edge wipe (BEW) detection system incorporating features of the present invention. An illumination source 2 illuminates the OPC device 10. At least one optical sensor 4 is positioned to view the illuminated OPC 10. A controller 6 connectable to the optical sensor senses manufacturing defects in the OPC device 10. In addition, the controller 6 is connectable to a database 8 containing threshold information for classifying the OPC 10 under test. The controller is also connectable to a monitoring device 9 such as an audible alarm or visual display capable of alerting a user when a defect occurs. Although the present invention will be described with reference to the embodiments shown in the drawings, it should be understood that the present invention can be embodied in many alternate forms of embodiments.

Figure 2:
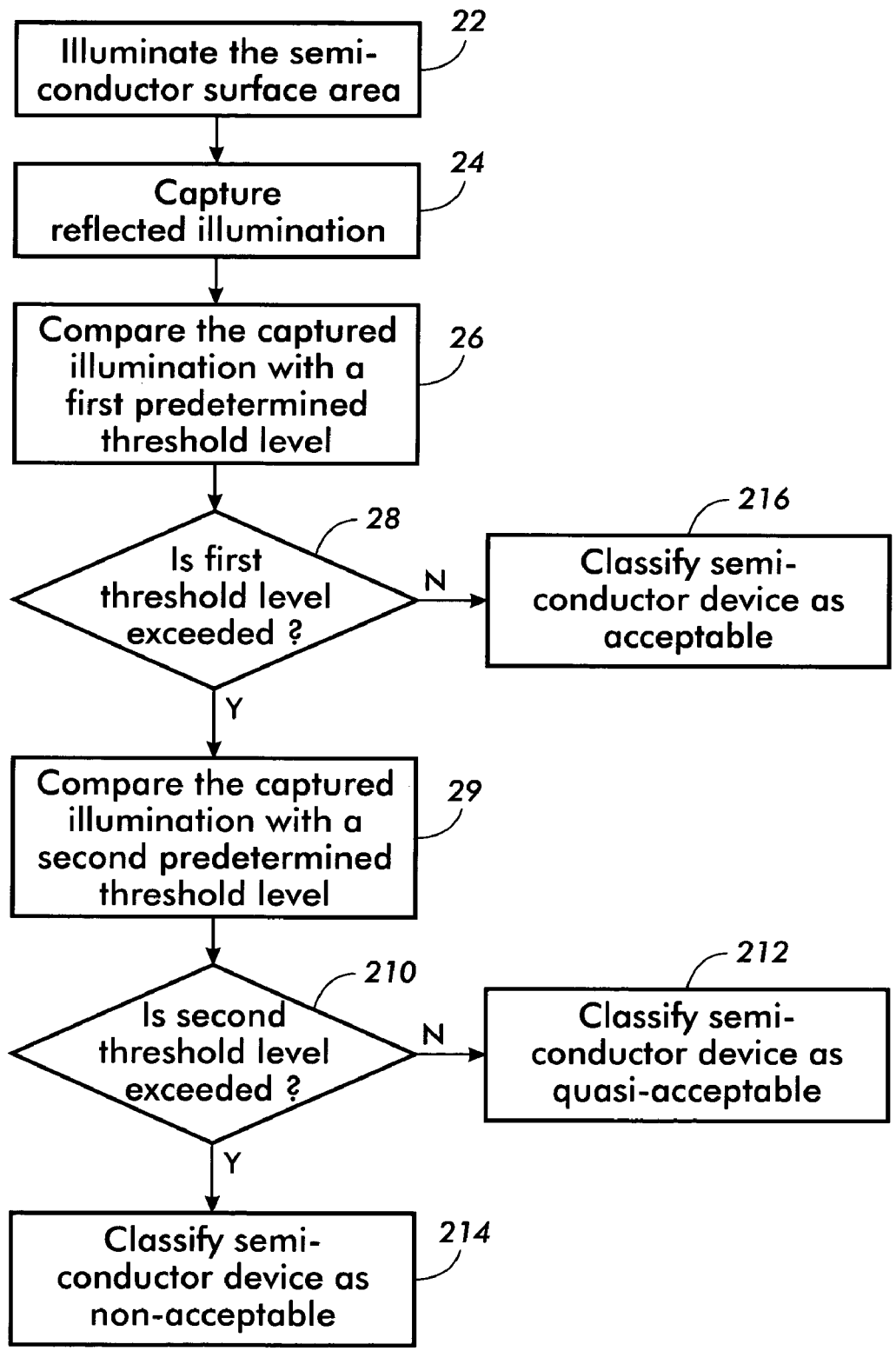
FIG. 2 is a method flow chart of one embodiment of the invention showing the steps for classifying the bottom area as acceptable, non-acceptable, or quasi-acceptable.
Figure 5:
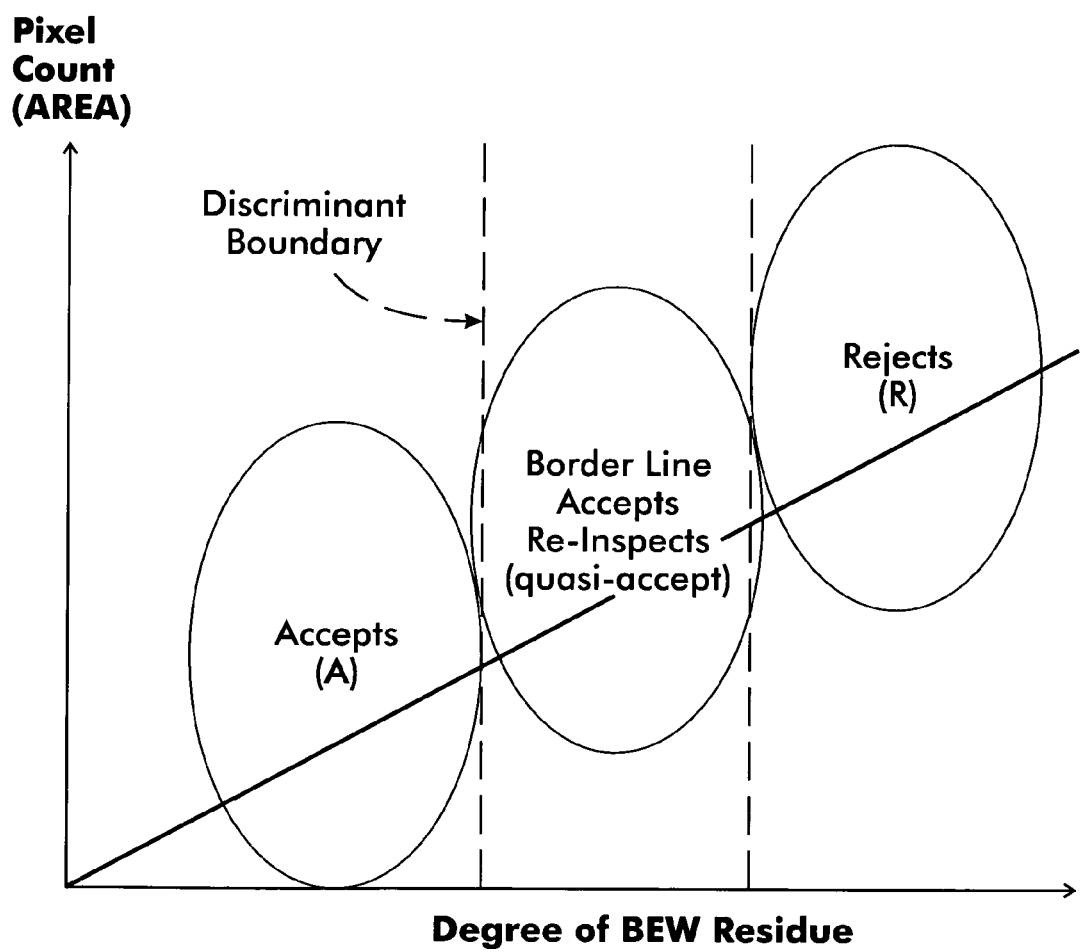
FIG. 5 is a graph illustrating the relations between threshold levels and degree of BEW residue.

Referring now to FIGS. 2 and 5; in FIG. 2 there is shown a method flow chart of one embodiment of the invention showing the steps for classifying the bottom area 12 of a OPC as acceptable, non-acceptable, or quasi-acceptable. First, the bottom edge area 12 of the OPC is illuminated 22 with a suitable illuminating device. Some examples of illuminating devices are light emitting diodes (LEDs), LASERs, or an emitter capable of emitting electromagnetic radiation of one or more wavelengths (i.e., a white light source). The reflected illumination from the bottom edge area 12 of the OPC is captured 24, where capturing the reflected illumination may be any suitable method for converting illumination intensity to a reference voltage or digital signal. The captured illumination is compared 26 with a predetermined threshold level to determine 28 if a first threshold level has been exceeded. If the first threshold has not been exceeded the OPC is classified as acceptable 216. If the first threshold has been exceeded the captured illumination is compared 29 with a second threshold level. If the captured illumination exceeds 210 the second threshold level the OPC is classified as non-acceptable 214 otherwise the OPC is classified as quasi-acceptable 212.

Figure 3:
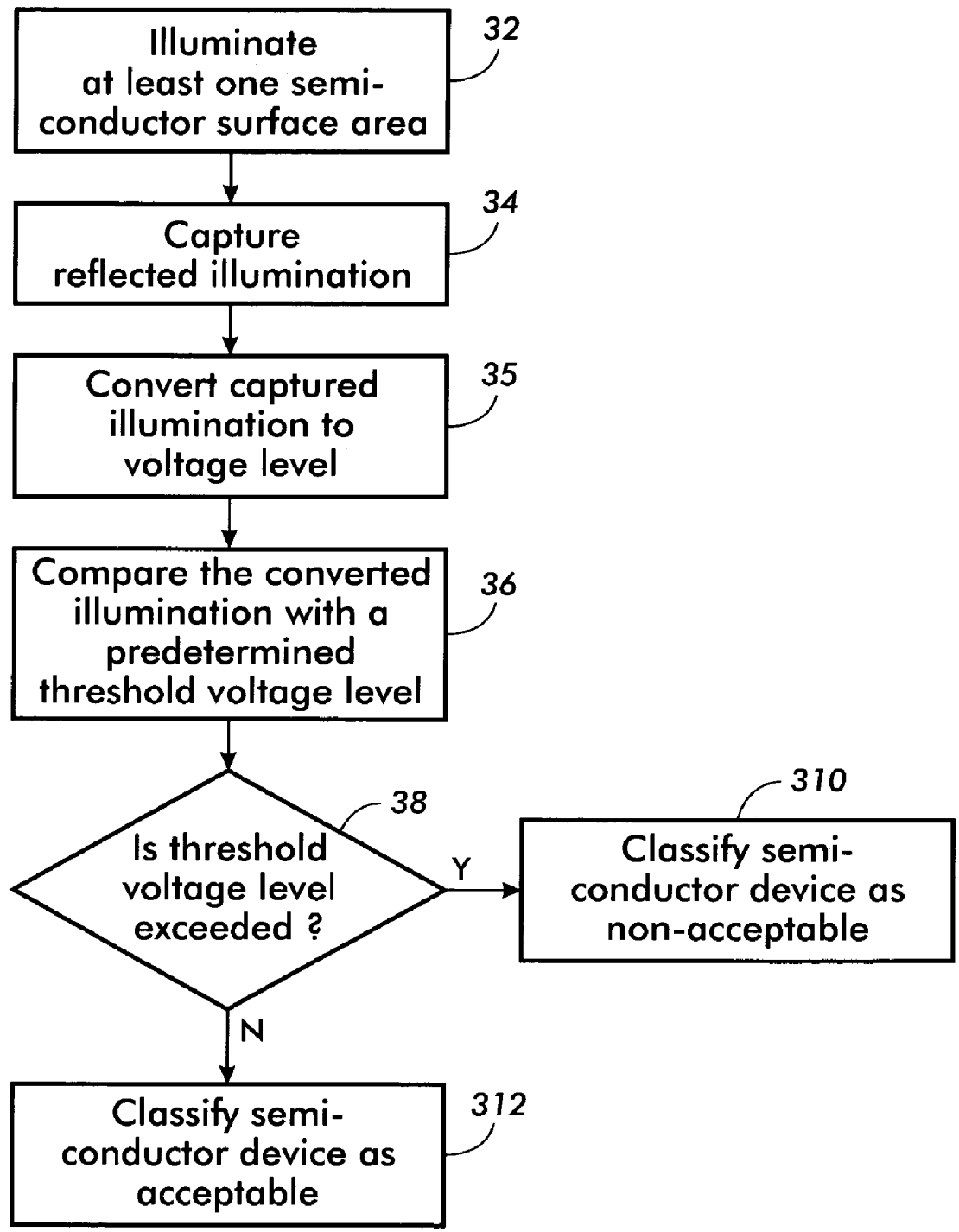
FIG. 3 is a detailed method flow chart corresponding to the method flow chart shown in FIG. 2 of one embodiment of the invention showing the steps for classifying the bottom area as acceptable or non-acceptable.
Figure 3A:
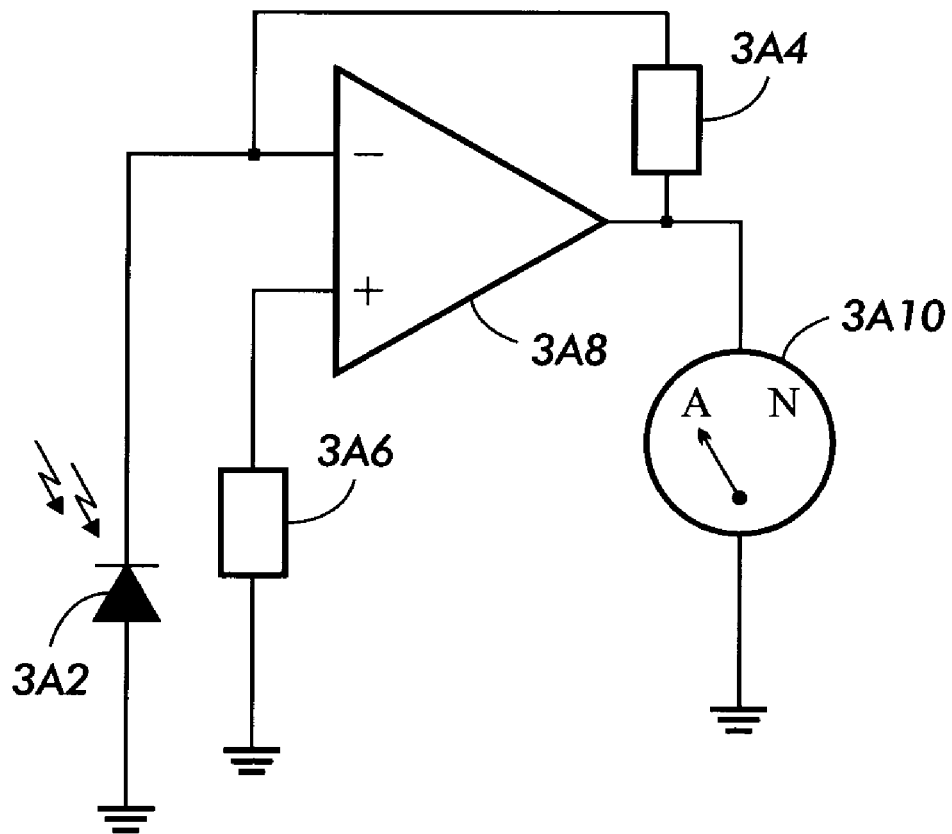
FIG. 3A is a schematic diagram of a circuit for implementation of the method shown in FIG. 3.

Referring now to FIG. 3 and there is shown a detailed method flow chart, corresponding to the method flow chart shown in FIG. 2, of one embodiment of the invention showing the steps for classifying the bottom area 12 as acceptable or non-acceptable; in FIG. 3A there is shown a schematic diagram of one implementation of a circuit for implementing the method shown in FIG. 3. First the OPC bottom area 12 is illuminated 32 and reflected illumination is captured 34, and converted 35 to a voltage by a semiconductor device such as a photodiode 3A2. The converted voltage is compared 36 to a predetermined voltage level after being amplified by an amplifier comprising a feedback resistor 3A4, an input resistor 3A6, and an operational amplifier 3A8. The predetermined voltage level may be set by reference to a known good OPC device with acceptable bottom edge residue. If the converted voltage exceeds 38 the predetermined voltage level as measured by voltmeter 3A10 the OPC device is classified 310, by 3A10 as non-acceptable; otherwise the device is classified as acceptable 312.

Figure 4:
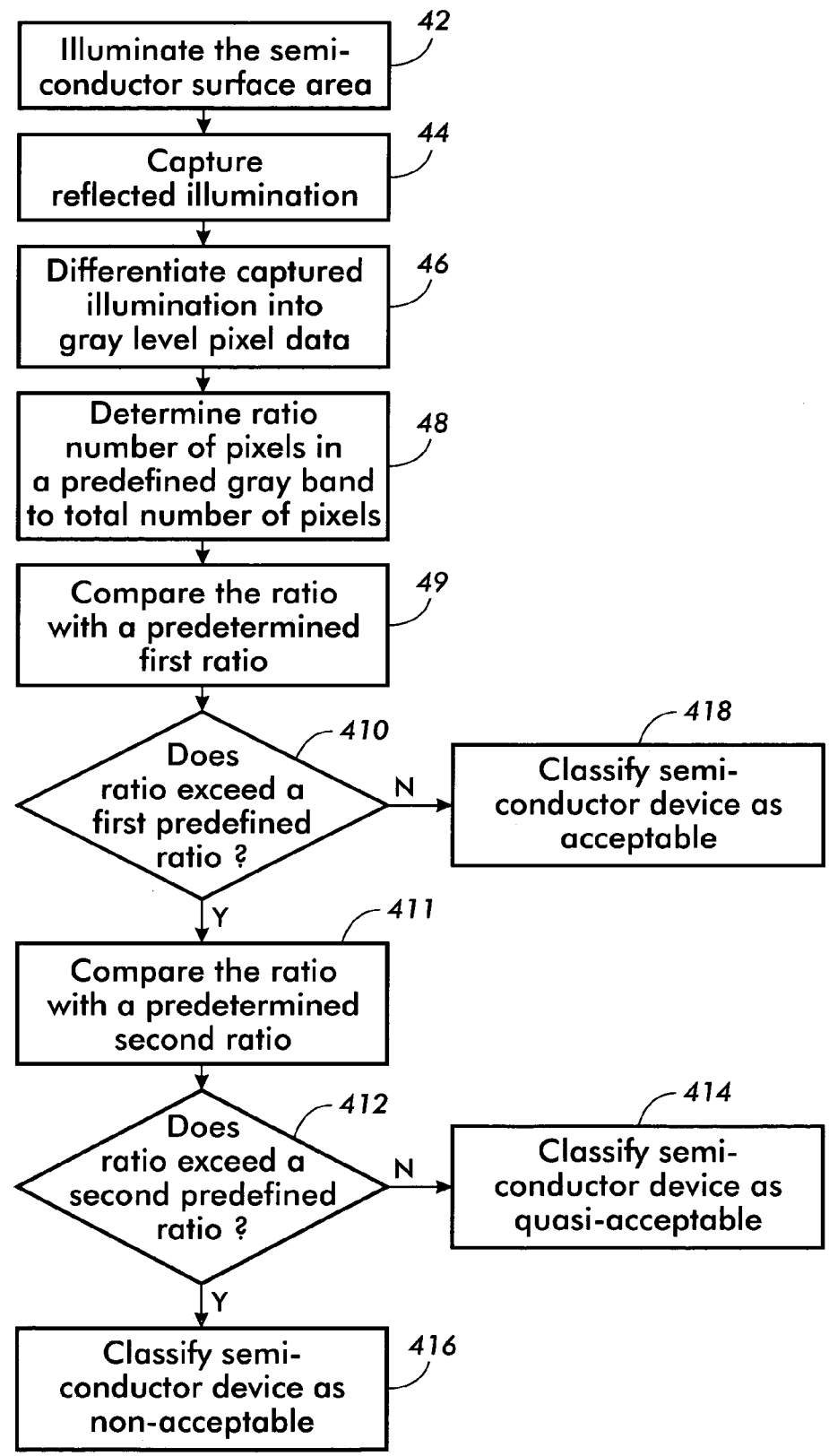
FIG. 4 is a detailed method flow chart of one embodiment of the invention corresponding to the method flow chart shown in FIG. 2, showing the steps for classifying the bottom area as acceptable, quasi-acceptable, or non-acceptable.

Referring now to FIG. 4 there is shown a detailed method flow chart of one embodiment of the invention showing the steps for classifying the bottom area 12 as acceptable, quasi-acceptable, or non-acceptable. First, the bottom area 12 of the OPC is illuminated 42 and reflected illumination is captured 44 by a charge coupled device (CCD) such as a digital camera. Through well known digital techniques the captured illumination is differentiated 46 into gray level pixel data or matrix cells. Dark areas of the bottom edge portion of the OPC due to BEW residue will correspond to dark pixels while lighter areas of the bottom edge portion will correspond to lighter pixels. A first threshold ratio is predetermined by determining a number of allowable dark pixels to the total number of pixels 48. For example, if a certain band is comprised of five dark pixels and the total number of pixels is fifty, the threshold ratio is one tenth or 0.1. The measured ratio of the device under test is then compared 49 with the first predefined threshold ratio that may be stored in a data storage area. If the ratio is determined 410 to have not exceeded the first predefined threshold ratio the OPC is classified as acceptable 418. If the ratio is determined 410 to have exceeded the first predefined ratio then a second comparison to a second predefined ratio is made 411. If the ratio is determined 412 to have exceeded the second predefined ratio the part is classified as non-acceptable 416; otherwise the part is classified as quasi-acceptable 414. For determining trends and maintenance requirements the classification of each OPC may be stored in the data storage area.

Thus the invention advantageously increases productivity and improves product quality by early inspection and detection of manufacturing defects early in the manufacturing process. It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A system for optically sensing manufacturing defects in organic photo conductor (OPC) devices, the system comprising:
    an illumination source for illuminating the OPC device;
    at least one optical sensor positioned to view the illuminated OPC, wherein the optical sensor provides a band of captured illumination with gray level picture data of a plurality of distinguishable pixels which are darker pixels or lighter pixels; and
    a controller connectable to the optical sensor for determining a ratio of a number of distinguishable pixels to a total number of pixels in the band, the controller comprising a threshold detector for sensing, based on said ratio, bottom edge wipe (BEW) manufacturing defects in the OPC device.

2. A system as in claim 1 wherein the illumination source comprises a light emitting diode (LED).

3. A system as in claim 1 wherein the illumination source comprises a LASER.

4. A system as in claim 1 wherein the illumination source comprises:
    an emitter, wherein the emitter emits electromagnetic radiation of at least one wavelength.

5. A system as in claim 1 wherein the at least one optical sensor comprises a charge coupled device (CCD) camera.

6. A system as in claim 1 wherein the controller is associated with a data storage area, wherein the data storage area is usable to store predetermined threshold values and classification results.

7. A system as in claim 1 wherein the threshold detector comprises an array of pixels and the controller further comprises a pixel counter for counting.

8. A system as in claim 1 wherein the controller is associated with a monitoring device for alerting a user.

9. A system as in claim 8 wherein the monitoring device further comprises a visual display monitor.

10. A system as in claim 8 wherein the monitoring device further comprises an audio monitor.

11. A method for optically classifying residues on at least one bottom edge area of an organic photo conductor (OPC) device, the method comprising the steps of:
    illuminating the at least one bottom edge area of the OPC device;
    capturing reflected illumination from the at least one illuminated bottom edge area of the OPC device, the step of capturing including a step of providing a band of captured illumination having gray level picture data of a plurality of distinguishable pixels which are darker pixels or lighter pixels;
    comparing the captured reflected illumination with at least one threshold level, the step of comparing including a step of determining a ratio of a number of distinguishable pixels to a total number of pixels in the band; and
    classifying the at least one bottom edge area of the OPC device based upon the comparison of the captured reflected illumination with the at least one threshold level.

12. A method as in claim 11 wherein the step of illuminating the at least one bottom edge area of the OPC device further comprises the step of illuminating the OPC bottom edge area with electromagnetic radiation of at least one wavelength.

13. A method as in claim 11 wherein the step of capturing reflected illumination from the at least one illuminated bottom edge area of the OPC device further comprises the step of digitizing the captured reflected illumination.

14. A method as in claim 11 wherein the step of capturing reflected illumination from the at least one illuminated bottom edge area of the OPC device further comprises the step of converting the captured reflected illumination to an analog signal.

15. A method as in claim 11 wherein the step of comparing the captured reflected illumination with at least one threshold level further comprises the step of comparing the captured reflected illumination with a predetermined pixel count.

16. A method as in claim 11 wherein the step of comparing the captured reflected illumination with at least one threshold level further comprises the step of comparing the captured reflected illumination with a predetermined analog voltage level.

17. A method as in claim 11 wherein the step of classifying the at least one bottom edge area of the OPC device further comprises the step of classifying the at least one bottom edge area as acceptable or alternatively as non-acceptable.

18. A method as in claim 11 wherein the step of classifying the at least one bottom edge area of the OPC device further comprises the step of classifying the at least one bottom edge area as one of acceptable, non-acceptable, and quasi-acceptable.

19. A method for optically classifying residues on at least one bottom edge area of an Organic Photo Conductor (OPC) device, the method comprising the steps of:
- illuminating the at least one bottom edge area of the OPC device;
- capturing reflected illumination from the at least one illuminated bottom edge area of the OPC device, the step of capturing including a step of providing a band of captured illumination having gray level picture data of a plurality of distinguishable pixels which are darker pixels or lighter pixels;
- comparing the captured reflected illumination with at least one threshold level, the step of comparing including a step of determining a ratio of a number of distinguishable pixels to a total number of pixels in the band; and
- classifying the at least one bottom edge area of the OPC device based upon the comparison of the captured reflected illumination with the at least one threshold level;
- wherein the step of comparing the captured reflected illumination with at least one threshold level further comprises the step of comparing the captured reflected illumination with a predetermined pixel count; and
- the step of comparing the captured reflected illumination with a predetermined pixel count further comprises the step of comparing the captured reflected illumination with a predetermined gray level pixel count.

20. A method for optically discriminating an Organic Photo Conductor (OPC) device, the method comprising the steps of:
- illuminating a bottom edge area of the OPC device;
- positioning an optical sensor to view the illuminated OPC bottom edge area, the optical sensor providing a band of captured illumination having gray level picture data of a plurality of distinguishable pixels which are darker pixels or lighter pixels; and
- providing a controller connectable to the optical sensor, the controller having a threshold discriminator that determines a ratio of a number of distinguishable pixels to a total number of pixels in the band for classifying the OPC device.

21. A method as in claim 20 wherein the step of illuminating the bottom edge area of the OPC device further comprises illuminating the bottom edge area of the OPC device with a visible light source.

22. A method as in claim 20 wherein the step of positioning the optical sensor to view the illuminated OPC bottom edge area further comprises positioning a charge coupled device (CCD) camera.

23. A method for optically discriminating an Organic Photo Conductor (OPC) device, the method comprising the steps of:
- illuminating a bottom edge area of the OPC device;
- positioning an optical sensor to view the illuminated OPC bottom edge area, the optical sensor providing a band of captured illumination having gray level picture data of a plurality of distinguishable pixels which are darker pixels or lighter pixels; and
- providing a controller connectable to the optical sensor, the controller having a threshold discriminator that determines a ratio of a number of distinguishable pixels to a total number of pixels in the band for classifying the OPC device;
- wherein the step of providing the controller connectable to the optical sensor further comprises the steps of:
- providing a gray level band discriminator;
- comparing the ratio of a number of pixels within a predetermined gray level band to a total number of gray level pixels to a predetermined ratio; and
- classifying the OPC device as acceptable, non-acceptable, or quasi-acceptable based upon said comparison.

24. A system for optically sensing a manufacturing defect in an organic photo conductor (OPC) device, the system comprising:
- a camera positioned to view a bottom edge wipe (BEW) region of the OPC device, wherein the camera provides an image of the BEW region with gray level picture data having a plurality of pixels including darker gray-level pixels and lighter gray-level pixels; and
- a controller for processing the picture data of the image, the controller determining a band of pixels having a value of gray-level darkness, and wherein the controller provides a ratio of a number of pixels in the band to a total number of pixels in the image, a magnitude of the ratio serving as a measure of the defect.

25. A system as in claim 24 further comprising a source of illumination for illuminating the OPC device, the camera being responsive to illumination reflected by the OPC device, and wherein the controller comprises a threshold detector for sensing the value of said ratio to establish the presence of the defect.

26. A method for optically classifying residues on a bottom edge wipe (BEW) region of an organic photo conductor (OPC) device, the method comprising the steps of:
- providing an image of a BEW region of the OPC device, wherein the image of the BEW region presents gray level picture data having a plurality of pixels including darker gray-level pixels and lighter gray-level pixels;
- processing the picture data of the image by determining a band of pixels having a value of gray-level darkness, and wherein the processing includes a further step of providing a ratio of a number of pixels in the band to a total number of pixels in the image, a magnitude of the ratio serving as a measure of BEW defects.

27. A method as in claim 26, further comprising the steps of:
- illuminating the BEW region of the OPC device, wherein the step of providing the image includes a capturing of illumination reflected from the BEW region, and the step of processing the data includes a step of comparing the captured reflected illumination with a threshold level to determine said ratio; and
- classifying the residue of the BEW region of the OPC device based upon a comparison of the captured reflected illumination with the threshold level.

* * * * *